United States Patent [19]

Niemers et al.

[11] 4,344,955
[45] * Aug. 17, 1982

[54] PENICILLIN 1,1-DIOXIDES

[75] Inventors: Ekkehard Niemers; Hans-Bodo König; Wilfried Schröck; Karl G. Metzger, all of Wuppertal, Fed. Rep. of Germany

[73] Assignee: Bayer Aktiengesellschaft, Leverkusen, Fed. Rep. of Germany

[*] Notice: The portion of the term of this patent subsequent to Aug. 17, 1999, has been disclaimed.

[21] Appl. No.: 158,975

[22] Filed: Jun. 12, 1980

[30] Foreign Application Priority Data

Jun. 27, 1980 [DE] Fed. Rep. of Germany ....... 2925963

[51] Int. Cl.³ .................... A61K 31/43; C07D 499/72
[52] U.S. Cl. ................................ 424/271; 260/239.1; 424/226; 424/248.55; 424/251; 424/263; 424/267; 424/270; 424/248.54; 424/450
[58] Field of Search .................... 260/239.1; 424/270, 424/271, 248.54, 248.55, 226, 250, 251, 263, 267, 248.53

[56] References Cited

U.S. PATENT DOCUMENTS 3,197,466 7/1965 Chow et al. .................... 260/239.1
3,536,698 10/1970 Chauvette et al. ............... 260/239.1

OTHER PUBLICATIONS

Tetrahedron Letters, No. 9, pp. 381–385, (1962).
J. Org. Chem., 28, pp. 1927–1928, (1963).
J. Org. Chem., 38, pp. 940–943, (1973).
J. Chem. Soc. Perkin I, pp. 1772–1775, (1976).

Primary Examiner—Natalie Trousof
Assistant Examiner—Vera C. Clarke
Attorney, Agent, or Firm—Sprung, Horn, Kramer & Woods

[57] ABSTRACT

Anti-bacterially active penicillin 1,1-dioxides of the formula

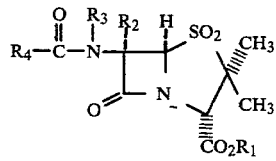

or a salt thereof, in which
$R_1$ denotes a hydrogen atom or an ester-forming radical,
$R_2$ denotes a hydrogen atom or optionally substituted alkoxy group,
$R_3$ denotes a hydrogen atom, $COR_4$, $SO_2$-alkyl, $SO_2$-aryl or an optionally substituted alkyl group, but $R_2$ and $R_3$ do not simultaneously denote hydrogen atoms, and
$R_4$ denotes a hydrogen atom or any of many possible organic radicals.

The compounds are also inhibitors of β-lactamases so they can be used in conjunction with β-lactamase-susceptible antibiotics. They are useful in fighting bacterial infection, in promoting animal growth and in preserving various materials.

9 Claims, No Drawings

PENICILLIN 1,1-DIOXIDES

The present invention relates to certain new penicillin 1,1-dioxide compounds, to processes for their production and to their use as medicaments in human medicine and veterinary medicine and as feed additives, and in particular their use as β-lactamase inhibitors.

1,1-Dioxides of various penicillins are described in J. Org. Chem. 28, 1927–1928, J. Org. Chem. 38, 940–943, J. Chem. Soc. 1976, 1772–1775, Tetrahedron Letters No. 9 (1962), 381 and in U.S. Pat. No. 3,197,466 and 3,536,698.

According to the present invention we provide compounds which are penicillin 1,1-dioxides of the general formula

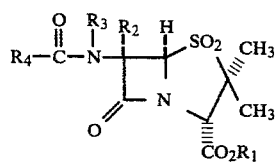

or a salt thereof, in which $R_1$ denotes a hydrogen atom or an ester-forming radical, $R_2$ denotes a hydrogen atom or an optionally substituted alkoxy group, $R_3$ denotes a hydrogen atom, —$COR_4$, —$SO_2$-alkyl, —$SO_2$-aryl or an optionally substituted alkyl group, but $R_2$ and $R_3$ do not simultaneously denote hydrogen atoms, and $R_4$ denotes a hydrogen atom, an optionally substituted alkyl group, an optionally substituted alkenyl group, an optionally substituted cycloalkyl group, an optionally substituted cycloalkenyl group, an optionally substituted cycloalkadienyl or aralkyl group, an optionally substituted alkoxy, aralkoxy, aryl, aryloxy or heterocyclyl radical or a radical of the general formula

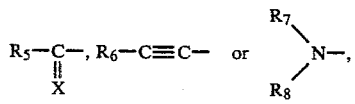

$R_5$ denotes a hydrogen atom, an optionally substituted alkyl group, an optionally substituted alkoxy, aryloxy or aryl group, an optionally substituted cycloalkyl group, an optionally substituted cycloalkenyl group, an optionally substituted cycloalkadienyl group or an optionally substituted alkenyl, aralkyl or heterocyclyl radical, $R_6$ denotes a hydrogen atom or an optionally substituted alkyl or aryl group, $R_7$ and $R_8$ independently denote a hydrogen atom, an optionally substituted alkyl group, an optionally substituted alkenyl or aryl group, an optionally substituted aralkyl group, an optionally substituted heterocylyl radical, an optionally substituted cycloalkyl group, an optionally substituted cycloalkenyl group or an optionally substituted cycloalkadienyl group, or $R_7$ and $R_8$, together with the nitrogen atom to which they are bonded, denote a 5-membered to 7-membered saturated or unsaturated heterocyclic ring which is optionally interrupted by further hetero-atoms, and X denotes an oxygen atom, $R_9$—N or

in which $R_9$ denotes a hydroxyl group, an optionally substituted alkoxy group, a heterocyclyl radical or a radical of the general formula

in which $R_7$ and $R_8$ independently have the meanings given above, and $R_{10}$ and $R_{11}$ independently denote a hydrogen atom, an optionally substituted alkyl, aryl or heterocyclyl radical, a carboxyl group or a functional derivative of a carboxyl group.

Examples of ester-forming radicals $R_1$ are optionally substituted alkyl and optionally substituted aralkyl, aryl and heterocyclyl.

In the general formula (I), optionally substituted alkyl of $R_1$, $R_2$, $R_3$, $R_4$, $R_5$, $R_6$, $R_8$, $R_{10}$ and $R_{11}$ and in —$SO_2$-alkyl of $R_3$ is straight-chain or branched alkyl with preferably 1 to 6, especially 1 to 4, carbon atoms. Examples which may be mentioned are optionally substituted methyl, ethyl, n- and i-propyl and n-, i- and t-butyl.

Optionally substituted alkenyl of $R_4$, $R_5$, $R_7$ and $R_8$ is straight-chain or branched alkenyl with preferably 2 to 6, especially 2 to 4, carbon atoms. Examples which may be mentioned are optionally substituted vinyl, propen-1-yl, propen-2-yl, buten-3-yl and buten-2-yl-.

Optionally substituted cycloalkyl, cycloalkenyl and cycloalkadienyl of $R_4$, $R_5$ $R_7$ and $R_8$ is monocyclic, bicyclic or tricyclic and preferably contains 3 to 10, especially 3, 5 or 6, carbon atoms. Examples which may be mentioned are optionally substituted cyclopropyl, cyclobutyl, cyclopentyl, cyclopentenyl, cyclohexyl, cyclohexenyl, cyclohexadienyl, cycloheptyl, bicyclo[2.2.1]-heptyl, bicyclo-[2.2.2]-octyl and adamantyl.

Optionally substituted aryl of $R_1$, $R_4$, $R_5$, $R_6$, $R_7$, $R_8$, $R_{10}$ and $R_{11}$ and in $SO_2$-aryl of $R_3$, and aryloxy of $R_4$ and $R_5$, is aryl, or aryloxy, with preferably 6 to 10 carbon atoms in the aryl part. Examples which may be mentioned are optionally substituted phenyl or naphthyl. Substituents in the phenyl ring are in the o-, m- or p-position.

Optionally substituted aralkyl of $R_1$, $R_4$, $R_5$, $R_7$ and $R_8$ and aralkoxy of $R_4$ is aralkyl or aralkoxy which is optionally substituted in the aryl part and/or alkyl part and has preferably 6 or 10, especially 6, carbon atoms in the aryl part and preferably 1 to 4, especially 1 or 2, carbon atoms in the alkyl part, it being possible for the alkyl part to be straight-chain or branched. Examples which may be mentioned are optionally substituted benzyl and phenylethyl.

Optionally substituted heterocyclyl of $R_1$, $R_4$, $R_5$, $R_7$, $R_8$, $R_9$, $R_{10}$ and $R_{11}$ is a hetero-paraffinic, hetero-aromatic or hetero-olefinic 5-membered to 7-membered, preferably 5-membered or 6-membered, ring with preferably 1 to 3, especially 1 or 2, identical or different hetero-atoms. Hetero-atoms are oxygen, sulphur or nitrogen. Examples which may be mentioned are optionally substituted thienyl, furyl, oxazolyl, isoxazolyl, thiazolyl, isothiazolyl, pyrrolyl, imidazolyl, pyrazolyl, oxdiazolyl, thiadiazolyl, triazolyl, sydnonyl, oxtriazolyl, thiatriazolyl, tetrazolyl, pyridyl, pyrazinyl, pyrimidinyl, tetrahydrofuranyl, dioxanyl, pyrrolidinyl, piperidinyl, morpholinyl, pyron-2-yl and pyron-4-yl.

The above-mentioned alkyl, alkenyl, cycloalkyl, cycloalkadienyl, aryl, aralkyl, aryloxy and aralkoxy can carry one or more, preferably 1 to 3, especially 1 or 2, identical or different radicals, preferably those defined as $R_{12}$ below.

Very particularly preferred radicals are the radicals mentioned which are unsubstituted or contain one substituent $R_{12}$.

Heterocylyl can contain one or more, preferably 1 to 3, in particular 1 or 2, identical or different radicals, preferably those defined as $R_{13}$ below. A very particularly preferred radical is heterocyclyl which is unsubstituted or contains one substituent $R_{13}$.

In the following explanations, the expression "lower alkyl" in all cases, also in connection with other atoms or groups bonded to an alkyl moiety (for example lower alkoxy, NCON-(lower alkyl))denotes straight-chain or branched alkyl with preferably 1 to 6, especially 1 to 4, carbon atoms. Examples which may be mentioned are optionally substituted methyl, ethyl, n- and i-propyl and n-, i- and t-butyl. "Lower alkyl" can be substituted by 1 to 5, in particular 1 to 3, identical or different halogen atoms, halogen atoms being, preferably, fluorine, chlorine and bromine, especially fluorine and chlorine. Trifluoromethyl, chloro-difluoromethyl, bromomethyl, 2,2,2-trifluoroethyl and pentafluoroethyl may be mentioned as examples.

$R_{12}$ denotes halogen (preferably fluorine, chlorine, bromine or iodine, and in particular fluorine, chlorine or bromine); amino; mono-lower alkylamino (preferably ethylamino or, especially methylamino); di-lower alkylamino (preferably diethylamino or especially, dimethylamino); pyrrolidyl; piperidyl; HCO—NH—; lower alkyl—CO—NH—, (preferably CH$_3$—CO—NH—); H—CO—N—(lower alkyl), (preferably H—CO—N(CH$_3$)— or H—CO—N(C$_2$H$_5$)—); lower alkyl—CO—N(lower alkyl)— (preferably CH$_3$—CO—N(CH$_3$)—); (lower alkyl)$_2$C=N—; lower alkyl—SO$_2$—NH— (preferably C$_2$H$_5$—SO$_2$—NH— or especially, CH$_3$—SO$_2$—NH—); lower alkyl—SO$_2$—N (lower alkyl)— (preferably CH$_3$—SO$_2$—N(CH$_3$)—); HO—SO$_2$—NH—; HO—SO$_2$—N(lower alkyl)— (preferably HO—SO$_2$—N—(CH$_3$)— or HO—SO$_2$—N(C$_2$H$_5$)—); amidino; (lower alkyl)$_2$—N—CH=N— (especially (CH$_3$)$_2$N—CH=N—);

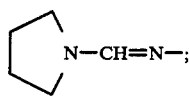

guanido; nitro; azido; hydroxyl; lower alkoxy (preferably C$_2$H$_5$—O— or especially CH$_3$O—); H—CO—O—, lower alkyl—CO—O— (preferably CH$_3$—CO—O, C$_2$H$_5$—CO—O— or (CH$_3$)$_3$C—CO—O—); lower alkyl—O—CO—O—, (preferably CH$_3$—O—CO—O—, C$_2$H$_5$—O—CO—O— or (CH$_3$)$_3$C—O—CO—O—); H$_2$N—CO—O—; lower alkyl—NH—CO—O— (preferably CH$_3$—NH—CO—O— or C$_2$H$_5$—NH—CO—O—); (lower alkyl)$_2$N—CO—O— (preferably (CH$_3$)$_2$N—CO—O— or (C$_2$H$_5$)$_2$N—CO—O—);

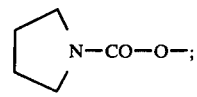

H$_2$N—SO$_2$—O—; lower alkyl—NH—SO$_2$—O— (preferably CH$_3$—NH—SO$_2$—O— or C$_2$H$_5$—NH—SO$_2$—O—); (lower alkyl)$_2$N—SO$_2$—O— (preferably (CH$_3$)$_2$N—SO$_2$—O— or (C$_2$H$_5$)$_2$N—SO$_2$—O—); HOOC—; H$_2$N—CO—; (lower alkyl)$_2$N—CO— (in particular (CH$_3$)$_2$N—CO— or (C$_2$H$_5$)$_2$N—CO—); OHC—; HO—SO$_2$—O—; HS—; lower alkyl—S— (preferably CH$_3$—S—, CF$_3$—S—, C$_2$H$_5$—S— or (CH$_3$)$_2$CH—S—);

lower alkyl—S— (preferably CH$_3$—S— or C$_2$H$_5$—S—);
∥                              ∥              ∥
O                              O              O HO$_3$S—; lower alkyl—SO$_2$— (preferably CH$_3$—SO$_2$—, CF$_3$SO$_2$— or C$_2$H$_5$—SO$_2$—); H$_2$N—SO$_2$—; lower alkyl—NH—SO$_2$—, (preferably CH$_3$—NH—SO$_2$— or C$_2$H$_5$—NH—SO$_2$—); (lower alkyl)$_2$ N—SO$_2$— (preferably (CH$_3$)$_2$N—SO$_2$— or (C$_2$H$_5$)$_2$N—SO$_2$—);

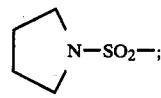

HO—SO$_2$—S—; phenyl or phenoxy.

Alkyl of $R_1$ is preferably also substituted by heterocyclyl, preferably furyl, thienyl, pyridyl or 2-oxobenzimidazolinyl; lower alkylcarbonyl (especially acetyl); benzoyl; lower dialkylamino-lower alkoxycarbonyloxy (especially dimethylamino- or diethylamino-C$_1$-C$_2$-alkoxycarbonyloxy); morpholino-; piperidino- or pyrrolidino-C$_1$-C$_2$-alkoxycarbonyloxy; lower alkoxycarbonylamino; or lower alkylcarbonylthio.

In the case where $R_{13}$ is on one or more carbon atoms in the heterocyclyl radical, $R_{13}$ preferably denotes lower alkyl (preferably ethyl, or isopropyl or especially methyl); the trifluoromethyl group; halogen (preferably fluorine, chlorine or bromine); amino; lower alkylamino (preferably CH$_3$—NH— or C$_2$H$_5$—NH—); di-lower alkylamino (preferably (CH$_3$)$_2$N— or (C$_2$H$_5$)$_2$N—); formylamino; acetylamino; CH$_3$—O—CO—NH— or C$_2$H$_5$O—CO—NH; CH$_3$—SO$_2$—NH—; hydroxyl; methoxy or ethoxy; methylthio or ethylthio; CH$_3$—SO$_2$—; CH$_3$—SO—; HOOC—; HO$_3$S—; HCO—; lower alkyl—CO— (preferably CH$_3$—CO—); lower alkyl—O—CO— (preferably CH$_3$—O—CO— or C$_2$H$_5$O—CO—); or —CN.

In the case where $R_{13}$ in a nitrogen-containing heterocylyl radical is a substituent on one or more nitrogen atoms, $R_{13}$ preferably denotes lower alkyl (preferably propyl or isopropyl, or especially, methyl or ethyl); the group —C≡N; —CHO; —COO—lower alkyl (preferably —COO—CH$_3$, —COOC$_2$H$_5$, —COOCH(CH$_3$)$_2$ or —COO—C(CH$_3$)$_3$); —CO—NH$_2$; —CO—NH—lower alkyl (preferably —CO—NH—CH$_3$, —CO—N-H—C$_2$H$_5$ or —CO—NH—CH—(CH$_3$)$_2$); or —CO—lower alkyl (preferably —CO—CH$_3$, —COC$_2$H$_5$ or —CO—CH(CH$_3$)$_2$).

Optionally substituted alkoxy of $R_2$, $R_4$, $R_5$ and $R_9$ is, for example, alkoxy which has 1 to 6, especially 1 to 3, carbon atoms and can be monosubstituted or polysubstituted, preferably monosubstituted, by $R_{12}$ as defined above.

Functional derivatives of the carboxyl group of $R_{10}$ and $R_{11}$ are ester groups as defined above for $R_1$, carboxylic acid amide groups, it being possible for the nitrogen atom to be substituted by $R_7$ and $R_8$ as defined above, cyano and corresponding thioanalogues.

Examples of heterocyclic radicals which $R_7$ and $R_8$ can form together with the nitrogen atom are pyrrolidinyl, piperidinyl, morpholinyl, piperazinyl and N-lower alkylpiperazinyl.

Preferred compounds of the present invention are those of the general formula

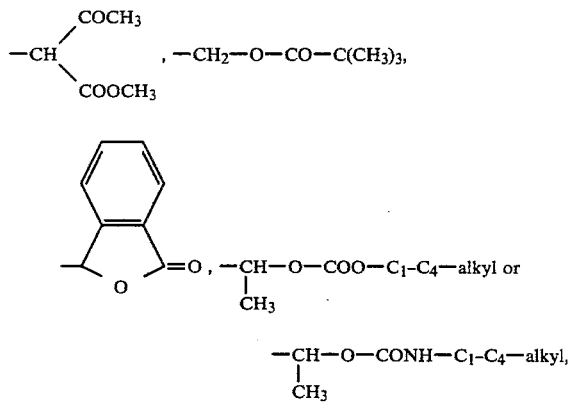

in which $R_{14}$ denotes a hydrogen atom, a sodium ion,

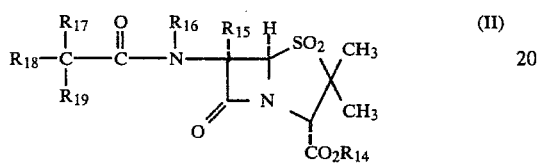

$R_{15}$ denotes a hydrogen atom or a methoxy group, $R_{16}$ denotes a hydrogen atom or an acetyl, benzoyl or methyl group, but $R_{15}$ and $R_{16}$ do not simultaneously denote hydrogen atoms, $R_{17}$ and $R_{18}$ independently denote a hydrogen atom, an optionally substituted $C_1$ to $C_4$ alkyl group, an optionally substituted $C_1$ to $C_4$ alkoxy group or both together with the carbon atom to which they are bonded denote a dioxacyclopentane or dioxacyclohexane ring and $R_{19}$ denotes an optionally substituted $C_1$ to $C_4$ alkyl group or an optionally substituted $C_1$ to $C_4$ alkoxy group or a phenyl, furyl, thienyl, methylisoxazolyl or iminothiazolyl radical.

Surprisingly, the compounds according to the invention exhibit a considerably more powerful inhibiting action on β-lactamases than the penicillin 1,1-dioxides known from the state of the art. The compounds according to the invention thus represent an enrichment of the range of medicaments.

According to the present invention we further provide a process for the production of compounds of the invention in which (a) a compound of the general formula

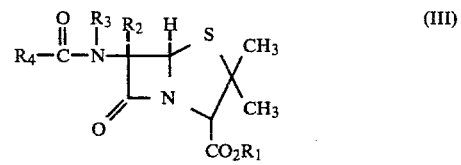

in which $R_1$, $R_2$, $R_3$ and $R_4$ have the meanings indicated above, is oxidized in a solvent, or (b) a 6-aminopenicillanic acid 1,1-dioxide of the general formula

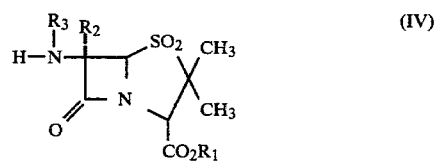

or a salt or an ester thereof, or a derivative thereof activated on the amino group, in which $R_1$, $R_2$, $R_3$ and $R_4$ have the meanings indicated above, is reacted with a compound of the general formula

or a reactive carboxylic acid derivative or a salt thereof, $R_4$ having the abovementioned meaning.

Substituted penicillins of the formula (III) used as starting compounds in reaction variant (a) are known and can be prepared by known processes, for example by acylation of 6-aminopenicillanic acid or esters thereof.

Possible solvents for reaction variant (b) are, in particular, polar solvents, for example, water, acetic acid and tetrahydrofuran and mixtures of these three. The reaction temperatures are in general between $-20°$ and $+50°$ C., preferably between $0°$ and $20°$ C. The reaction is in general carried out under normal pressure. The pH value of the reaction solution is in general between 2 and 8, preferably between 3.5 and 7.5.

In each case stoichiometric amounts of the reactants are preferably employed in carrying out the reaction variant (a). However, it is in all cases possible to add one of the reactants in excess, preferably the oxidizing agent. The reaction products are worked up by the methods customary in preparative organic chemistry.

The oxidation is preferably carried out with the following oxidizing agents: potassium permanganate, ozone, hydrogen peroxide, hydrogen peroxide in the presence of catalytic amounts of ammonium molybdate, hydrogen peroxide in glacial acetic acid, organic peracids (such as peracetic acid), chromium trioxide, ruthenium tetroxide, nitric acid, and N-chlorosuccinimide in methanol/water.

If free amino groups are present in the compounds of the formula (III) used as the starting material, these are in general provided with protective groups, such as benzyloxycarbonyl, tert.-butoxycarbonyl or β-dicarbonyl derivatives, by methods customary in peptide chemistry before the oxidation and these groups are split off again in customary manner after the oxidation.

A suitable reactive derivative of the compound (IV) used as a starting compound in reaction variant (b) can be, for example, an imino derivative of the Schiff's base type, or an amine tautomer which is formed by reacting the compound (IV) with a carbonyl compound, and furthermore a silyl derivative, which is formed by reacting the compound (IV) with a silyl compound, such as bis-(trimethylsilyl)-acetamide, trimethylsilylacetamide, and furthermore a derivative which is formed by reacting the compound (IV) with phosphorus trichloride or phosgene.

A suitable salt of the compound (IV) can be an acid addition salt, for example an organic acid salt, such as an acetate, maleate, tartrate, benzenesulphonate or toluenesulphonate, or an inorganic acid salt, such as a hydrochloride, hydrobromide, sulphate or phosphate, a metal salt, such as a sodium, potassium, calcium or magnesium salt, an ammonium salt or an inorganic amine salt, such as a triethylamine or dicyclohexylamine salt.

The suitable reactive carboxylic acid derivative of the compound (V) can be an acid halide, an acid anhydride, an activated amide or an activated ester. Examples which may be mentioned of such derivatives of the compound of formula (V) are an acid chloride, acid azide, mixed acid anhydride with an acid such as a substituted phosphoric acid, for example a dialkylphosphoric acid, phenylphosphoric acid, diphenylphosphoric acid, dibenzylphosphoric acid or a halogenated phosphoric acid, a dialkylphosphoric acid, sulphurous acid, thiosulphuric acid, sulphuric acid, an alkylcarbonic acid, an aliphatic carboxylic acid, for example pivalic acid, pentanecarboxylic acid, isopentanecarboxylic acid, 2-ethylbutyric acid or trichloroacetic acid, or an aromatic carboxylic acid, for example benzoic acid, or a symmetric acid anhydride, an activated amide formed with imidazole, dimethylpyrazole, triazole or tetrazole or an activated ester, such as a cyanomethyl, methoxymethyl, dimethyliminomethyl, vinyl, propargyl, p-nitrophenyl, 2,4-dinitrophenyl, trichlorophenyl, pentachlorophenyl, mesylphenyl, phenylazophenyl, phenylthio, p-nitrophenylthio, p-cresylthio, carboxymethylthio, pyranyl, pyrridyl, piperidyl, or 8-quinolylthio ester or an ester with N,N-dimethylhydroxylamine, 1-hydroxy-2-(1H)pyridone, N-hydroxysuccinimide, N-hydroxyphthalimide or 1-hydroxy-6-chloro-1H-benzotriazole.

The salts of the compound (V) can be salts with an inorganic base, for example alkali metal salts, such as sodium salts or potassium salts, or alkaline earth metal salts, such as calcium salts or magnesium salts, a salt with an organic base, such as trimethylamine, triethylamine or pyridine, or a salt with an acid, such as hydrochloric acid or hydrobromic acid.

The reaction variant (b) is as a rule carried out in a conventional solvent, such as water, acetone, dioxane, acetonitrile, chloroform, methylene chloride, ethylene chloride, tetrahydrofuran, ethyl acetate, N,N-dimethylformamide or pyridine, or any other organic solvent which does not have an adverse effect on the reaction, in particular a polar solvent. Of these solvents, the hydrophilic solvents can be used as mixtures with water.

If the compound (V) is used in the reaction in the form of a free acid or in the form of its salt, the reaction is preferably carried out in the presence of a conventional condensing agent, such as N,N-dicyclohexylcarbodiimide, N-cyclohexyl-N'-morpholinoethylcarbodiimide, N-cyclohexyl-N'-(4'-diethylaminocyclohexyl)-carbodiimide, N,N-diethylcarbodiimide, N,N-diisopropylcarbodiimide, N-ethyl-N'-(3-dimethylaminopropyl)-carbodiimide, N,N-carbonyl-bis-(2-methylimidazole), pentamethyleneketene-N-cyclohexylimide, diphenylketene-N-cyclohexylimine, ethoxyacetylene, ethylpolyphosphate, isopropylpolyphosphate, diethyl phosphorochloridite, phosphorus oxychloride, phosphorus trichloride, thionyl chloride, oxalyl chloride, triphenylphosphine, N-ethyl-7-hydroxybenzisoxazolium fluoborate, N-ethyl-5-phenylisoxazolium 3'-sulphonate, 1-(p-chlorobenzenesulphonyloxy)-6-chloro-1H-benzotriazole, a so-called Vilsmeier reagent, such as (chloromethyl)dimethylammonium chloride (prepared by reacting dimethylformamide with thionyl chloride or phosgene) or a compound which is prepared by reacting dimethylformamide with phosphorus oxychloride.

The reaction variant (b) can also be carried out in the presence of an inorganic or organic base, for example an alkali metal hydroxide, an alkali metal dicarbonate, an alkali metal carbonate, an alkali metal acetate, a trialkylamine, pyridine, an N-alkylmorpholine, an N,N-dialkylbenzylamine or an N,N-dialkylaniline. If the base of the condensing agent is liquid, it can also be used as the solvent. The reaction temperature is not critical and the reaction is as a rule carried out with cooling or at room temperature.

If the compounds of the formula (IV) used as a starting material for reaction variant (b) contain free amino groups, these are in general first provided with protective groups, for example benzyloxycarbonyl or tert.-butoxycarbonyl, by a method customary in peptide chemistry. When the reaction has ended, these protective groups are split off again in the customary manner.

The 6-aminopenicillanic acid 1,1-dioxide used as the starting material can be prepared by a procedure in which 6-aminopenicillanic acid is first converted into 6-benzyloxycarbonylaminopenicillanic acid by reaction with carbobenzoxy chloride, the 6-benzyloxycarbonylaminopenicillanic acid is then oxidized with potassium permanganate, and the carbobenzoxy protective group is then split off hydrogenolytically in the presence of a palladium catalyst.

The compounds of the present invention display an antimicrobial activity, coupled with low toxicity. These properties enable them to be used as chemotherapeutic active compounds in medicine and as substances for preserving inorganic and organic materials, especially organic materials of all kinds, for example polymers, lubricants, paints, fibers, leather, paper and timber, and foodstuffs and water.

Examples of micro-organisms against which the active compounds of the formula (I) display an action are: Micrococcaceae, such as Staphylococci, for example *Staphylococcus aureus, Staphylococcus epidermidis, Staphylococcus aerogenes* and *Gasskya tetragena;* Lactobacteriacea, such as Streptococci, for example *Streptococcus pyogenes,* and *Diplococcus pneumoniae;* Neisseriaceae, such as Neisseriae, for example *Neisseria gonorrhoeae, Neisseria meningitidis, Neisseria catarrhalis* and *Neisseria flava;* and Bacillacea, such as aerobic sporeforming Bacillaceae, for example *Bacillus anthracis, Bacillus subtilis* and *Bacillus cereus.*

The above list of pathogens is purely illustrative.

As stated above, the invention also relates to the use in human and veterinary medicine in combating bacterial diseases, of the compounds of the invention.

The present invention provides a pharmaceutical composition containing as active ingredient a compound of the invention in admixture with a solid or liquefied gaseous diluent, or in admixture with a liquid diluent other than a solvent or a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampules or suppositories comprising a compound of the invention.

"Medicament" as used in this specification means physically discrete coherent portions suitable for medical administration. "Medicament in dosage unit form" as used in this specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical composition according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters such as $C_{14}$-alcohol with $C_{16}$-fatty acid) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminum hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example ground nut oil), glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitan esters), microcrystalline cellulose, aluminum metahydroxide, bentonite, agar-agar and tragacanth or mixtures thereof.

All the pharmaceutical compositions according to the invention can also contain coloring agents and preservatives as well as perfumes and flavoring additions (e.g. peppermint oil and eucalyptus oil) and sweetening agents (e.g. saccharin).

The pharmaceutical compositions according to the invention generally contain from 0.1 to 99.5%, usually from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampules. Some of these forms may be made up for delayed release of the active ingredient. Some, such as capsules, include a protective envelope which renders the portions of the medicament physically discrete and coherent.

The preferred daily dose for administration of the medicaments of the invention is 500 mg to 10 g of active ingredient.

The product of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating (including prevention, relief and cure of) the above-mentioned diseases in human and non-human animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously), rectally or locally, preferably orally or parenterally, especially intravenously or intramuscularly. Preferred pharmaceutical compositions and medicaments are therefore those adapted for administration such as oral or parenteral administration. Administration in the method of the invention is preferably oral or parenteral administration.

In general it has proved advantageous to administer amounts of from 5 mg to 1,000 mg/kg, preferably 10 mg to 200 mg/kg, of body weight per day, optionally in the form of several individual administrations, to achieve effective results. An individual administration preferably contains the active compound or compounds according to the invention in amounts of 1 mg to 250 mg/kg, in particular 10 mg to 100 mg/kg, of body weight. Nevertheless, it can at times be necessary to deviate from those dosage rates, and in particular to do so as a function of the nature and body weight of the human or animal subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, while in other cases the upper limit mentioned must be exceeded to achieve the desired results. Where larger amounts are administered it can be advisable to divide these into several individual administrations over the course of the day.

The new penicillanic acid 1,1-dioxide derivatives of the present invention are distinguished by an antibacterial action, which has been tested in vivo and in vitro and by oral resorbability.

In order to broaden the spectrum of action and to achieve an increase in action, especially in the case of bacteria which form β-lactamase, the penicillanic acid 1,1-dioxide derivatives according to the invention can be combined with other antimicrobially active compounds, for example with penicillins.

In order to broaden the spectrum of action and to achieve an increase in action, the penicillanic acid 1,1-dioxide derivatives according to the invention can also be combined with aminoglycoside antibiotics, such as gentamicin, kanamicin, sisomicin, amikacim or tobramicin.

The penicillanic acid 1,1-dioxide derivatives according to the invention inactivate, by inhibition or destruction, the bacterial enzymes which split the β-lactam ring (β-lactamases). The degradation of other penicillins, for example of amoxycillin, piperacillin, mezlocillin, ampicillin, azlocillin, penicillin G, carbenicillin and ticarcillin, is thereby prevented, and on the one hand their activity is thereby retained and on the other hand their spectrum of action is extended to bacteria which produce β-lactamse.

In vitro experiments

The compound of Example 1, which can be regarded as a typical representative of the compounds according to the invention, was diluted with Müller-Hinton nutrient broth, with the addition of 0.1% of glucose, to a content of 100 μg/ml. In eace case, the nutrient solution contained $1 \times 10^5$ to $2 \times 10^5$ bacteria per ml. The small tubes containing this batch were each incubated for 24 hours and the degree of turbidity was then determined. Absence of turbidity indicates action. At a dosage of 1 μg/ml, the bacteria cultures inoculated with Staphylococcus aureus 133 were free from turbidity.

The following examples illustrate the process for the production of compounds of the present invention.

EXAMPLE 1

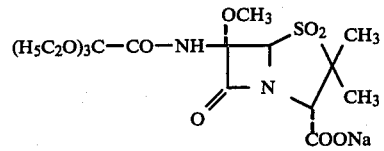

(a) 7.9 g of potassium triethoxy acetate were reacted with 4.23 ml of pivaloyl chloride in 70 ml of tetrahydrofuran at $-10°$ C. for 20 hours to produce the mixed anhydride of triethoxyacetic acid and pivalic acid.

(b) 6.5 g of 6-amino-6-methoxy-penicillanic acid in 60 ml of water were dissolved by bringing the pH to triethylamine. This was combined at 0° C. with the mixed anhydride product of (a), yielding 6-triethoxyacetamido-y-methoxy-penicillanic acid. Converted to the sodium salt, the yield was 12.5 g.

(c) 4 g of the sodium salt of 6-triethoxyacetamido-6-methoxy-penicillanic acid were dissolved in 40 ml of water and the pH was adjusted to 7 to 7.5. A solution of 1.9 g of potassium permanganate in 50 ml of water, and 0.66 ml of 85% strength phosphoric acid were then added dropwise at 0° C. in the course of about 20 minutes, during which the pH was kept at 6 to 7.5 by means of 10% strength phosphoric acid. The mixture was subsequently stirred for 10 minutes and any excess of potassium permanganate present was then removed by means of sodium bisulphite solution. The mixture was filtered over a filtration auxiliary, the material on the filter was rinsed with water, the combined aqueous filtrates were covered with a layer of ethyl acetate and the mixture was acidified to pH 2 at about 0° C. with dilute hydrochloric acid. The organic phase was separated off and the aqueous phase was extracted a further three times by shaking with ethyl acetate. The combined ethyl acetate extracts were extracted with water and the aqueous phase was then freeze-dried. Yield: 3.85 g.

The following substances can be prepared in the same manner:

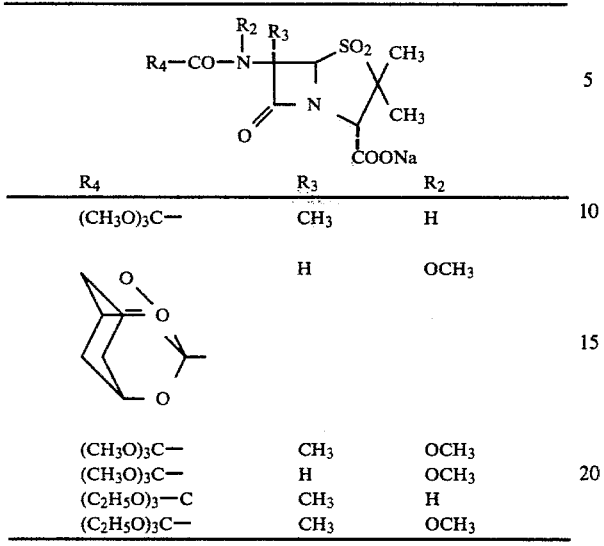

| R4 | R3 | R2 |
|---|---|---|
| (CH3O)3C— | CH3 | H |
| | H | OCH3 |
| (CH3O)3C— | CH3 | OCH3 |
| (CH3O)3C— | H | OCH3 |
| (C2H5O)3—C | CH3 | H |
| (C2H5O)3C— | CH3 | OCH3 |

EXAMPLE 2

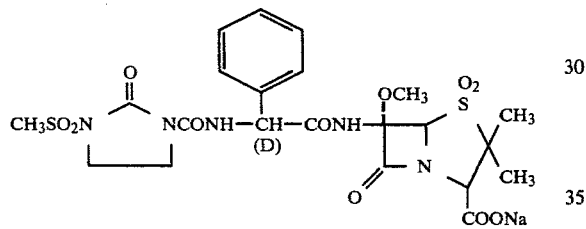

This penicillin S-dioxide was obtained, in the manner described in Example 1, as the acid in 83% yield from 8 g of sodium 6-α-methoxy-[D-α-[(2-oxo-3-mesylimidazolidin)-1-carboxamido]-benzylpenicillin, after acidification of the filtered and washed aqueous solution. The crude acid was dissolved in acetone, precipitated with water, filtered off and suspended in water, the suspension was adjusted to pH 7 with 2 N NaOH and the resulting aqueous solution was freeze-dried. Yield of sodium 6-α-methoxy-[D-α-[(2-oxo-3-methylimidazolindin)-1-carboxamido]-benzylpenicillin S-dioxides: 41%.

NMR signals at $\tau = 2.3$–2.9 (5H), 4.35 (1H), 4.75 (1H), 5.9 (1H), 6.15 (4H), 6.55 (3H), 6.7 (3H) and 8.65 ppm (6H).

The following substances could be prepared in the same manner:

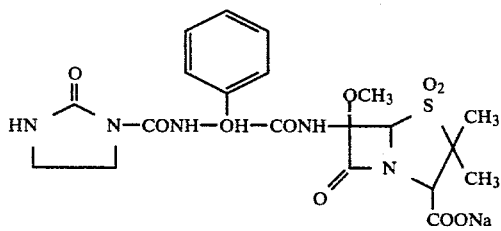

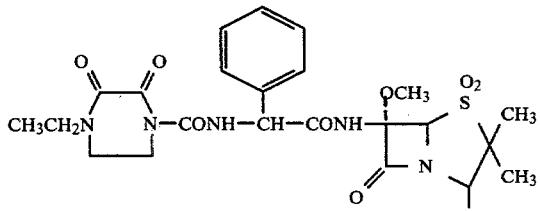

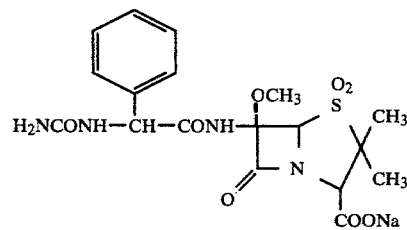

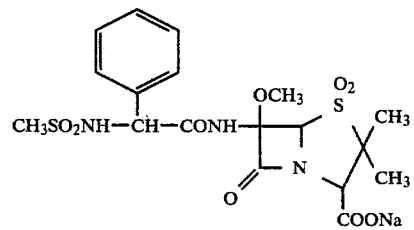

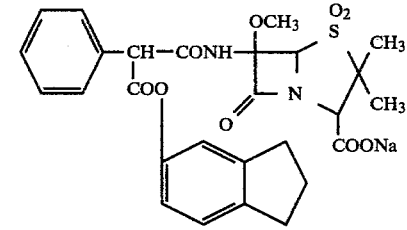

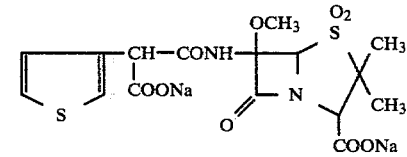

EXAMPLE 3

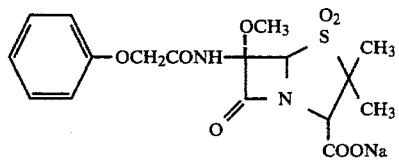

This penicillin S-dioxide was prepared in 70% yield from 4 g of 6-methoxy-penicillin V in the manner described in Example 1.

NMR signals at $\tau = 2.4$ (5H), 4.8 (1H), 5.6 (2H), 5.8 (1H), 6.6 (3H) and 8.7 ppm (6H).

The following substances could be prepared in the same manner:

[Structures shown for Example 4 series:
- PhCH₂CONH-, OCH₃ substituted penam S,S-dioxide, COONa
- CH₃CONH-, OCH₃ substituted penam S,S-dioxide, COONa
- PhO-CH(CH₂CH₃)-CONH-, OCH₃ substituted, COONa
- Cyclohexyl-CONH-, OCH₃ substituted, COONa
- (CH₃CO)₂N- substituted penam, COONa
- PhOCH₂CON(COCH₃)- substituted penam S,S-dioxide, COONa
- PhCH₂CON(COPh)- substituted penam S,S-dioxide, COONa]

EXAMPLE 4

[Structure: o-HOOC-C₆H₄-CONH- penam S,S-dioxide, COOH]

This penicillin S-dioxide was obtained, in the manner described in Example 1, in 59% yield from 7 parts by weight of o-carboxyphenylpenicillin, after evaporation of the ethyl acetate extract of the acidified auqeous solution.

NMR signals at $\tau = 2.0$–2.6 (4H), 4.15 (1H), 4.9 (1H), 5.4 (1H) and 8.45+8.6 ppm (6H).

IR bands at 3600–2100, 1800, 1715, 1330–1200 and 1116 cm$^{-1}$.

EXAMPLE 5

[Structure: penicillin S-dioxide with β-ethoxycarbonyl-carbamoyl substituent, COOH]

This penicillin S-dioxide was prepared in the manner described in Example 1 from 3 parts by weight of β-ethoxycarbonyl-carbamoylethylpenicillin and, after acidification of the aqueous solution, was taken up in ethyl acetate and precipitated, as the Na salt, from this mixture with sodium 2-ethylhexanoate and the Na salt was filtered off, washed with ether and dried in a desiccator. Yield: 70%.

IR bands at 1790, 1760, 1675, 1612, 1310, 1218, 1160, 1112 and 1032 cm$^{-1}$.

NMR signals at $\tau = 4.15$ (1H), 5.1 (1H), 5.8 (1H), 5.85 (2H), 7.1–7.6 (4H), 8.5 (3H), 8.65 (3H) and 8.75 ppm (3H).

EXAMPLE 6

[Structure: isoxazolyl-CONH- penam S,S-dioxide, CO₂H]

This penicillin S-dioxide was prepared in the manner described in Example 1.

Yield: 55%.

NMR (CD₃OD): 1.55 (s,3H), 1.65 (s,3H), 2.4 (s,3H), 4.3 (s,1H), 5.05 (d,1H), 6.1 (α,1H), and 6.95 (s,1H) ppm (δ scale).

Among the new penicillin 1,1-dioxide salts of the invention, those salts that are pharmaceutically acceptable are particularly important and are preferred.

The new free penicillin 1,1-dioxides of the general formula I and their salts can be interconverted in any suitable manner; methods for such interconversion are known in the art.

The present invention also comprises pharmaceutically acceptable bioprecursors of the active compounds of the present invention.

For the purrposes of this specification the term 'pharmaceutically acceptable bioprecursor' of an active compound of the invention means a compound having a structural formula different from the active compound but which nonetheless, upon administration to an animal or human being is converted in the patient's body to the active compound.

It will be appreciated that the instant specification and examples are set forth by way of illustration and not limitation, and that various modifications and changes may be made without departing from the spirit and scope of the present invention.

We claim:

1. A penicillin 1,1-dioxide of the formula $$R_4-\overset{O}{\overset{\|}{C}}-\overset{R_3}{\underset{|}{N}}-\overset{R_2}{\underset{|}{\underset{|}{C}}}\overset{H}{\underset{\underset{\overset{\|}{O}}{}}{\underset{|}{C}}}\overset{SO_2}{\underset{N}{\underset{|}{\underset{|}{C}}}}\overset{CH_3}{\underset{CH_3}{\underset{|}{\underset{|}{C}}}}$$
$$CO_2R_1$$

or a pharmaceutically acceptable salt thereof, in which
$R_1$ denotes a hydrogen atom or an ester-forming radical, $R_2$ denotes a hydrogen atom or optionally substituted alkoxy group, $R_3$ denotes a hydrogen atom, $COR_4$, $SO_2$-alkyl, $SO_2$-aryl or an optionally substituted alkyl group, but $R_2$ and $R_3$ do not simultaneously denote hydrogen atoms, and $R_4$ denotes a hydrogen atom, an optionally substituted alkyl group, an optionally substituted alkenyl group, an optionally substituted cycloalkyl group, an optionally substituted cycloalkenyl group, an optionally substituted cycloalkadienyl or aralkyl group, an optionally substituted alkoxy, aralkoxy, aryl, aryloxy or heterocyclyl radical or a radical of the formula $$R_5-\overset{}{\underset{\overset{\|}{X}}{C}}-, \quad R_6-C\equiv C- \quad \text{oder} \quad \overset{R_7}{\underset{R_8}{\diagdown N-,}}$$

$R_5$ denotes a hydrogen atom, an optionally substituted alkyl group, an optionally substituted alkoxy, aryloxy or aryl group, an optionally substituted cycloalkyl group, an optionally substituted cycloalkenyl group, an optionally substituted cycloalkadienyl group, or an optionally substituted alkenyl, aralkyl or heterocyclyl radical, $R_6$ denotes a hydrogen atom or an optionally substituted alkyl or aryl group, $R_7$ and $R_8$ independently denote a hydrogen atom, an optionally substituted alkyl group, an optionally substituted alkenyl or aryl group, an optionally substituted aralkyl group, an optionally substituted heterocyclyl radical, an optionally substituted cycloalkyl group, an optionally substituted cycloalkenyl group or an optionally substituted cycloalkadienyl group, or $R_7$ and $R_8$ together denote a heterocyclyl radical, and X denotes an oxygen atom, $R_9$—N or $$\overset{R_{10}}{\underset{R_{11}}{\diagdown C \diagup}}$$

in which $R_9$ denotes a hydroxyl group, an optionally substituted alkoxy group, a heterocyclyl radical or a radical of the formula $$\overset{R_7}{\underset{R_8}{\diagdown N}}$$

in which $R_{10}$ and $R_{11}$ independently denote a hydrogen atom, an optionally substituted alkyl, aryl or heterocyclyl radical, a carboxyl group or a functional derivative of a carboxyl group; the heterocyclyl radicals being selected from the group consisting of thienyl, furyl, oxazolyl, isoxazolyl, thiazolyl, isothiazolyl, pyrrolyl, imidazolyl, pyrazolyl, oxdiazolyl, thiadiazolyl, triazolyl, sydnonyl, oxtriazolyl, thiatriazolyl, tetrazolyl, pyridyl, pyrazinyl, pyrimidinyl, tetrahydrofuranyl, dioxanyl, pyrrolidinyl, piperidinyl, morpholinyl, pyron-2-yl and pyron-4-yl, and the optional substituents being selected from the group consisting of halogen; amino; mono-lower alkylamino; di-lower alkylamino; pyrrolidyl; piperidyl; HCO—NH—; lower alkyl—CO—NH—; H—CO—N— (lower alkyl); lower alkyl—CO—N(lower alkyl); (lower alkyl)$_2$C=N—; lower alkyl —SO$_2$—NH—; lower alkyl —SO$_2$—N (lower alkyl)—; HO—SO$_2$—NH—; HO—SO$_2$—N (lower alkyl); amidino; (lower alkyl)$_2$—N—CH=N—;

$$\overset{}{\underset{}{\diagup\diagdown}} N-CH=N=;$$

guanido; nitro; azido; hydroxyl; lower alkoxyl; H—CO—O—, lower alkyl—CO—O—; lower alkyl—O—CO—O—; H$_2$N—CO—O—; lower alkyl—NH—CO—O—; (lower alkyl)$_2$N—CO—O;

$$\overset{}{\underset{}{\diagup\diagdown}} N-CO-O-; \quad H_2N-SO_2-O-;$$

lower alkyl—NH—SO$_2$—O—; (lower alkyl)$_2$N—SO$_2$—O—; HOOC—; H$_2$N—CO—; (lower alkyl)$_2$—N—CO—; OHC—; HO—SO$_2$—O—; HS—; lower alkyl—S—;

$$\text{lower alkyl}-\overset{O}{\underset{\|}{S}}-;$$

HO$_3$S—; lower alkyl—SO$_2$— or H$_2$N—SO$_2$—; lower alkyl—NH—SO$_2$—; (lower alkyl)$_2$N—SO$_2$—;

$$\overset{}{\underset{}{\diagup\diagdown}} N-SO_2-;$$

HO—SO$_2$—S—; phenyl or phenoxy.

2. A compound or salt according to claim 1, of the formula

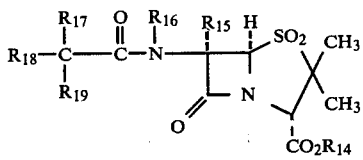

in which $R_{14}$ denotes a hydrogen, a sodium ion,

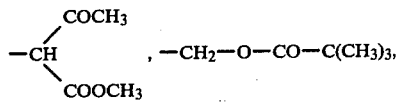

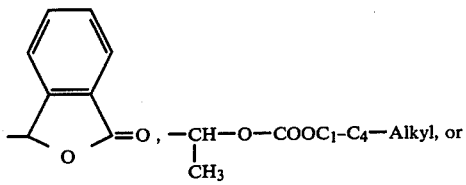

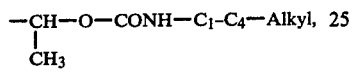

$R_{15}$ denotes a hydrogen atom or a methoxy group, $R_{16}$ denotes a hydrogen atom or an acetyl, benzoyl or methyl group, but $R_{15}$ and $R_{16}$ do not simultaneously denote hydrogen atoms, $R_{17}$ and $R_{18}$ independently denote a hydrogen atom, an optionally substituted $C_1$ to $C_4$ alkyl group, an optionally substituted $C_1$ to $C_4$ alkoxy group, or together with the carbon atom to which they are bonded, a dioxacyclopentane or dioxacyclohexane ring and $R_{19}$ denotes an optionally substituted $C_1$ to $C_4$ alkyl group or an optionally substituted $C_1$ to $C_4$ alkoxy, phenyl, furyl, thienyl, methylisoxazolyl or iminothiazolyl radical.

3. A compound according to claim 1, wherein such compound is

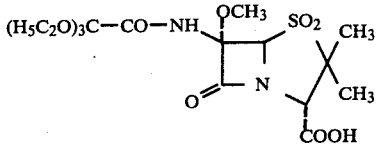

or a pharmaceutically acceptable salt thereof.

4. An anti-bacterial or growth promoting composition comprising an anti-bacterially or growth promoting effective amount of a compound or salt according to claim 1 in admixture with a diluent.

5. A composition according to claim 4 in unit dose form.

6. An anti-bacterial composition comprising an effective amount of a compound or salt according to claim 1 in admixture with a β-lactam antibiotic susceptible to β-lactamases.

7. A method of combating bacteria which comprises applying to such bacteria or a habitat thereof an anti-bacterially effective amount of a compound or salt according to claim 1.

8. A method of promoting the growth of animals which comprises administering to such animals a growth promoting effective amount of a compound or salt according to claim 1.

9. A method of combating bacteria which comprises applying to such bacteria or a habitat thereof an anti-bacterially effective amount of a compound or salt according to claim 3.

UNITED STATES PATENT AND TRADEMARK OFFICE
CERTIFICATE OF CORRECTION

PATENT NO. : 4,344,955
DATED : August 17, 1982
INVENTOR(S) : Ekkehard Niemers et al It is certified that error appears in the above-identified patent and that said Letters Patent is hereby corrected as shown below:

On the title page

(30) Priority Data

Delete "Jun. 27, 1980" and insert -- June. 27, 1979 --

Signed and Sealed this

Fourth Day of January 1983

[SEAL]

Attest:

Attesting Officer

GERALD J. MOSSINGHOFF

Commissioner of Patents and Trademarks